(12) United States Patent
Pisano et al.

(10) Patent No.: US 8,053,460 B2
(45) Date of Patent: Nov. 8, 2011

(54) INDOLE DERIVATIVES HAVING ANTITUMOR ACTIVITY

(75) Inventors: Claudio Pisano, Aprilia (IT);
Gianfranco Battistuzzi, Rome (IT);
Maria Di Marzo, Santa Maria a Vico Casera (IT); Giuseppe Giannini, Pomezia (IT); Mauro Marzi, Rome (IT); Loredana Vesci, Rome (IT); Franco Zunino, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 495 days.

(21) Appl. No.: 11/917,065

(22) PCT Filed: May 31, 2006

(86) PCT No.: PCT/EP2006/062798
§ 371 (c)(1),
(2), (4) Date: Feb. 15, 2008

(87) PCT Pub. No.: WO2006/131484
PCT Pub. Date: Dec. 14, 2006

(65) Prior Publication Data
US 2008/0207729 A1    Aug. 28, 2008

(30) Foreign Application Priority Data
Jun. 10, 2005 (IT) .................. 05012562.4

(51) Int. Cl.
*A61K 31/404* (2006.01)
*C07D 209/10* (2006.01)
(52) U.S. Cl. ........................ 514/414; 548/455
(58) Field of Classification Search ............ 548/455
See application file for complete search history.

(56) References Cited

U.S. PATENT DOCUMENTS

2003/0130335 A1 * 7/2003 Mjalli et al. .................. 514/414
2004/0053987 A1 * 3/2004 Giannini et al. ............. 514/414

FOREIGN PATENT DOCUMENTS

| WO | 99/00381 X | 1/1999 |
|----|------------|--------|
| WO | 02/36561 X | 5/2002 |
| WO | WO 03/032982 X | 4/2003 |
| WO | 2004/076386 X | 9/2004 |

OTHER PUBLICATIONS

Benghiat E et al "Multisubstrate Adducts as Potential Inhibitors of S-Adenosylmethionine Dependent Methylases: . . . " Journal of Medicinal chemistry, American Chemistry Society, Washington, US. vol. 26, No. 10, 1983, pp. 1470-1477.

Boettcher, H. et al.: "Synthesis and dopaminergic activity of some 3-(1,2,3,6-tetrahydro-1-pyridylalkyl) indoles. A novel conformational model to explain structure-activity relationship." J. Med. Chem. vol. 35, No. 22, 1992, pp. 4020-4026.

Tokmakov, G.P. et al: "Interaction of 3,4-dihydro-2H-thiopyan with phenylhydrazines. Synthesis of homothiotrypophols" Database CA Chemical Abstracts Service, Columbus, Ohio, US, (2005).

Kayumov, V. et al.: Indole derivatives. LXXXIV. Hydroxamic acids of teh indole series. Database CA Chemical Abstracts Service, Columbus, Ohio, US, (2005).

* cited by examiner

*Primary Examiner* — Shawquia Young
(74) *Attorney, Agent, or Firm* — Lucas & Mercanti LLP.

(57) ABSTRACT

Indole derivatives of Formula (I+A) having antitumor and chemosensitizing activity are described. Also described are pharmaceutical compositions containing the above-mentioned compounds, for the treatment of tumors.

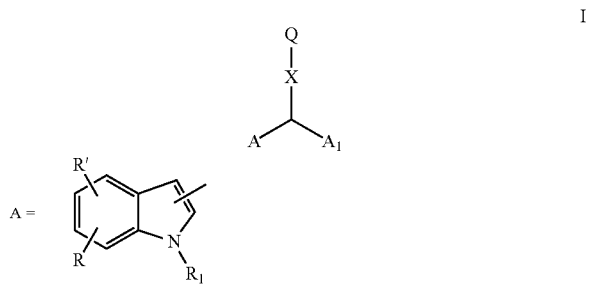

10 Claims, 1 Drawing Sheet

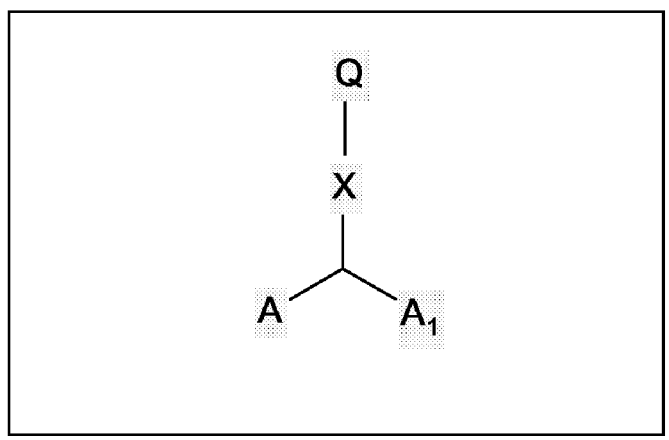
Formula I
where
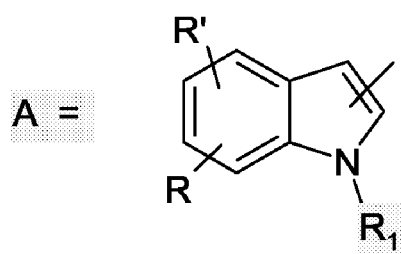

INDOLE DERIVATIVES HAVING ANTITUMOR ACTIVITY

FIELD OF THE INVENTION

The present invention relates to indole derivatives having antitumour activity as well as to the pharmaceutical compositions containing the above-mentioned compounds, for the treatment of tumours

BACKGROUND OF THE INVENTION

The therapy of tumours is being currently achieved by surgical intervention, radiation treatment and chemotherapy. The drawbacks of this latter are mainly due to the toxicity of the cytotoxic drugs, which is usually not limited to the cancer cells, and to the acquired resistance of the cancer cells to some of the most widely used drugs, which reduces the long-term efficacy of the therapy.

The elimination of the primary tumour by surgery is not always possible and in any case does not prevent the most metastasizing tumours, such as for example breast cancer or melanoma, to invade other target organs.

It has become evident that the therapy of the metastasizing tumours is unlikely to bring to the complete cure of the patient; therefore, the treatment with cytotoxic drugs is now seen as a palliative and life-prolonging method rather than a curative method. A chronic treatment with a drug having low toxicity would be preferable, while targeted to the control of the progression of the disease.

During the last years cancer drug development has moved from conventional cytotoxic chemotherapeutics to a more mechanism-based targeted approach towards the common goal of tumour growth arrest. The rapid progress in chromatin research and understanding epigenetic control has supplied a plethora of potential targets for intervention in cancer.

Histone deacetylases (HDACs) have been widely implicated in growth and transcriptional control, and inhibition of HDAC activity using small molecules causes apoptosis in tumour cells. Histone deacetylase inhibitors are now known to be potent inducers of growth arrest, differentiation, or apoptotic cell death in a variety of transformed cells in culture and in tumour bearing animals (Marks, P. A., Current Opinions in Oncology, 2001, Nov. 13 (6): 477-83; Marks, P., Nat. Rev. Cancer 2001 Dec. 1 (3):194-202).

On the other hand, as anticipated before, another very important and keenly perceived aspect of oncological therapy is the onset of resistance to the drug used by the tumour cells treated. The cells that develop resistance to a drug are often capable of resisting the effects of many other antitumour drugs, even if these are unrelated chemically or act with different mechanisms of action. (Annu. Rev. Med. 1991, 42: 277-286; Drugs of the Future 1997, 22: 653-660).

A number of tumours, such as, for instance, tumours of the adrenal cortex, colon, kidneys and jejunum and liver carcinoma manifest drug resistance right from the very start of treatment with antitumour drugs (Barrows, L. R. Antineoplastic and Immunoactive Drugs, 1995; 75; 1236-1262).

In other cases, the tumour cells acquire resistance in a manner similar to that of bacterial resistance to antibiotics. This type of resistance has genetic or epigenetic changes; these changes allow the daughter cells to proliferate in a milieu in which the antitumour agent is present.

Whatever the cause of the resistance, it leads to inefficacy of the antineoplastic treatment in the long term.

Patent application WO99/00381 describes bis-indole derivatives with antimetastatic activity.

Patent application WO02/36561, filed in the name of the applicant discloses compounds bis-heterocyclic compounds useful as antitumour agents.

In conclusion, in the oncology field there is a strongly perceived need for new compounds endowed with antitumour and/or chemosensitising activity, i.e. compounds which are active against drug-resistant tumours and/or capable of making known antitumour drugs active against tumours against which they were ineffective owing to the onset of the above-mentioned conditions of drug resistance.

DESCRIPTION OF THE INVENTION

We have found that a class of indole derivatives possess the requisites essential for such antitumour, antimetastatic and chemosensitizing activity.

The compounds of the present invention showed to be more potent than the homologue compounds described in the patent application WO02/36561, to inhibit the proliferation of NB4 promyelocytic leukaemia cells (see the results presented in Table 1 and Table 2 under the section Examples). These surprising anti-proliferative results, revealed for this new class of compounds an anticancer potentiality for the treatment of cancer patients resistant to the therapies currently used.

Therefore the main object of the present invention are the indole compounds of Formula (I) below, which are useful agents as antitumour, antimetastatic and chemosensitiser agents.

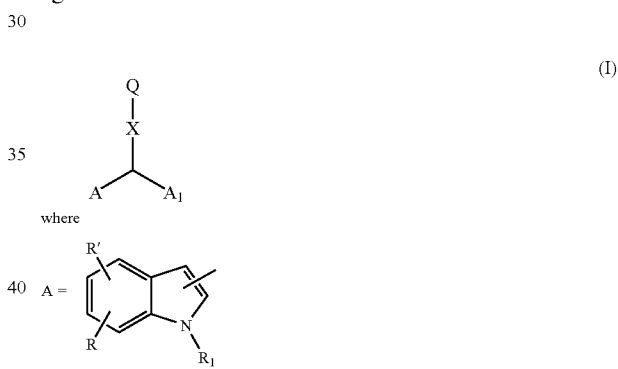

where $A_1$ is either H or A, wherein R, R' and $R_1$ are the same for both indole rings;

X is a saturated or unsaturated (alkenylene or alkynylene), linear or branched ($C_2$-$C_{10}$) alkylene, optionally substituted with OH, or a ($C_6$-$C_{12}$) aryl, ($C_3$-$C_{10}$) heteroaryl containing at least one heteroatom selected from N, O or S, wherein in the cyclic groups at least one of the —CH— is optionally substituted with C-halogen or C—($C_1$-$C_3$) alkyl;

Q=SH, COCONR$_2$R$_3$, COCF$_3$, or

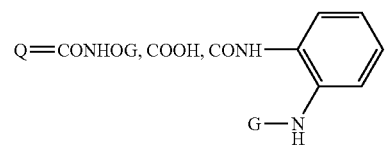

Q=CONHOG, COOH, CONH where,
G is either H or a glycosyl;
$R_2$, $R_3$ are the same or different and are either H or a $(C_1-C_4)$ alkyl;
$R_1$ is selected from the group consisting of H, $(C_1-C_4)$ alkyl, $(C_6-C_{12})$ aryl, $(C_6-C_{12})$ aryl-$(C_1-C_4)$ alkylene, $(C_1-C_4)$ alkanoyl and $(C_1-C_4)$-alkyl-$(C_6-C_{10})$-arylene;
R and R', the same or different, are selected from the group consisting of:
H;
saturated or unsaturated, linear or branched $(C_1-C_{10})$ alkyl, optionally substituted with a $(C_3-C_{10})$ heteroaryl or $(C_3-C_{10})$ heterocyclyl-$(C_1-C_4)$ alkylene, where the heterocycle contains at least one heteroatom selected from N, O or S, or with a group —$NR_5R_6$, where $R_5$, $R_6$ are the same or different and are H, linear or branched $(C_1-C_4)$ alkyl, $(C_1-C_4)$-alkanoyl;
$OR_4$ where $R_4$=H, $(C_1-C_4)$ alkyl, mesyl, tosyl, $(C_1-C_4)$ alkanoyl, glycosyl;
halogen, azide, nitro, nitrile and $NR_5R_6$.

The present invention also comprises tautomers, geometrical isomers, optically active forms as enantiomers, diastereomers and racemate forms, as well as pharmaceutically acceptable salts of the compounds of Formula (I).

Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

Within the framework of the present invention, examples of the linear or branched $(C_1-C_4)$ alkyl group, are understood to include methyl, ethyl, propyl and butyl and their possible isomers, such as, for example, isopropyl, isobutyl, and ter-butyl.

The term "alkylene" refers to a linear or branched chain divalent hydrocarbon radical. Examples of "alkylene" as used herein include, but are not limited to, methylene, ethylene, propane-1,3-diyl, propane-1,2-diyl and the like.

Examples of the $(C_6-C_{12})$ aryl or $(C_6-C_{12})$ aryl-$(C_1-C_4)$ alkyl group are phenyl, 1- or 2-naphthyl, anthracenyl, benzyl, 2-phenylethyl 1-phenylethyl, 3-phenylpropyl, 2-anthracenylpropyl, 1-anthracenylpropyl, naphthylmethyl, 2-naphthylethyl, 1-naphthylethyl, 3-naphthylpropyl, 2-naphthylpropyl, 1-naphthylpropyl.

As used herein, the term "$(C_3-C_6)$ heterocyclo" or the term "$(C_3-C_6)$ heterocyclyl" refers to a monovalent three to six-membered non-aromatic ring containing one or more heteroatomic substitutions independently selected from S, O, or N and having zero to five degrees of unsaturation. Examples of "heterocyclic" as used herein include, but are not limited to, tetrahydrofuryl, pyranyl, 1,4-dioxanyl, 1,3-dioxanyl, piperidinyl, pyrrolidinyl, tetrahydrothiopyranyl, tetrahydrothiophenyl, and the like.

As used herein, the term "$(C_3-C_6)$ heterocyclylene" refers to a divalent three to six membered non-aromatic heterocyclic ring radical containing one or more heteroatoms independently selected from S, O, or N and having zero to five degrees of unsaturation. Examples of "heterocyclylene" as used herein include, but are not limited to, tetrahydrofuran-2,5-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, and the like.

What is meant by halogen is fluorine, chlorine, bromine and iodine.

Examples of the glycosyl residue are 6-D-galactosyl and 6-D-glucosyl.

According to independently preferred embodiments of the invention, X is a saturated or unsaturated (alkenylene or alkynylene), linear $(C_2-C_{10})$ alkylene;
$A_1$ is A;

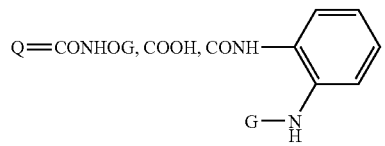

G, $R_1$, $R_2$ and $R_3$ are H;
and R and R' are the same or different and are H, linear $(C_1-C_{10})$ alkyl, optionally substituted with a $(C_3-C_{12})$ heteroaryl containing at least one heteroatom selected from N, O or S, or with a group —$NR_5R_6$ or $OR_4$ where $R_4$ is $(C_1-C_4)$ alkyl.

The following are some of the most preferred compounds according to the invention:
3-{4-[Bis-(1H-indol-3-yl)-methyl]-phenyl}-N-hydroxy-acrylamide (ST2887),
5,5-Bis-(1H-indol-3-yl)-pentanoic acid hydroxyamide (ST2743),
6,6-Bis-(1H-indol-3-yl)-hexanoic acid hydroxyamide (ST2754),
7,7-Bis-(1H-indol-3-yl)-heptanoic acid hydroxyamide (ST2741),
7,7-Bis-(4-fluoro-1H-indol-3-yl)-heptanoic acid hydroxyamide (ST3052),
7,7-Bis-(5-methyl-1H-indol-3-yl)-heptanoic acid hydroxyamide (ST3044),
7,7-Bis-(7-ethyl-1H-indol-3-yl)-heptanoic acid hydroxyamide (ST3126),
7,7-Bis-(7-methoxy-1H-indol-3-yl)-heptanoic acid hydroxyamide (ST3043),
8,8-Bis-(1H-indol-3-yl)-octanoic acid hydroxyamide (ST2889),
N-Hydroxy-4,4-bis-(1H-indol-3-yl)-butyramide (ST2408),
N-Hydroxy-6-(1H-indol-3-yl)-hexanamide (ST2995), 7,7-Bis-(5-morpholin-4-ylmethyl-3H-indol-3-yl)-heptanoic acid hydroxyamide (ST3307),
7-(1H-Indol-3-yl)-7-(1H-indol-2-yl)-heptanoic acid hydroxyamide (ST3292), and
7,7-Bis-(1H-indol-3-yl)-heptanoic acid (ST3127).

The experimental results obtained (reported in the section entitled "Examples") show that the compounds of Formula (I), both alone and in combination with other known antitumour drugs, are useful agents for the treatment of tumours.

A further object of the invention described herein are compounds with general Formula (I) and their use in the medical field.

A further object of the invention described herein is a pharmaceutical composition containing as active ingredient a compound of Formula (I) and at least a pharmaceutically acceptable excipient and/or diluent.

A further object of the invention described herein are compounds with general Formula (I) and a process for their preparation.

A further object of the invention described herein is a pharmaceutical composition containing as active ingredient a compound of Formula (I), for the treatment of a tumour pathology, in which the tumour is selected from the group consisting of sarcoma, carcinoma, carcinoid, bone tumour, neuroendocrine tumour, lymphoid leukaemia, acute promyelocytic leukaemia, myeloid leulaemia, monocytic leukaemia, megakaryoblastic leukaemia and Hodgkin's disease.

A further object of the invention described herein is a pharmaceutical composition containing as active ingredient a compound Formula (I), for the treatment of a tumour pathology, in which the tumour has shown drug resistance to the previous antibiotics used for its treatment, in which said compound of Formula (I) exerts a chemosensitising effect on said drug resistant tumour.

A further object of the invention described herein is a pharmaceutical composition containing as active ingredient a compound of Formula (I), in combination with one or more known antitumour agents, in which the antitumour compound is selected from the group consisting of alkylating agents, topoisomerase inhibitors, antitubulin agents, intercalating compounds, anti metabolites, natural products such as vinca alkaloids, epipodophyllotoxins, antibiotics, enzymes, taxans, and cytodifferentiating compounds. Among the cytodifferentiating antitumour agents the one preferred is all-trans retinoic acid.

Another object of the present invention is a process for preparing the pharmaceutical compositions, as explained before, comprising mixing the compound(s) of Formula (I) with the suitable excipient(s) and/or diluent(s).

A further object of the invention described herein is the use of a compound of Formula (I) for the preparation of a medicine for the treatment of a tumour pathology.

A further object of the invention described herein is the use of a compound of Formula (I) for the preparation of a medicine for the treatment of a tumour pathology in which the tumour has shown drug resistance to the previous antitumour drugs used for its treatment, in which said compound of Formula (I) exerts a chemosensitising effect on said drug-resistant tumour.

A further object of the invention described herein is the use of a compound of Formula (I), in combination with one or more known antitumour agents, for the preparation of a medicine for the treatment of tumour pathologies.

A further object of the invention described herein is the use of a compound of Formula (I) in combination with all-trans retinoic acid for the preparation of a medicine for the treatment of acute promyelocytic leukaemia.

Another object of the invention is a method of treating a mammal suffering from a tumour pathology, comprising administering a therapeutically effective amount of the compound(s) of Formula (I).

"Therapeutically effective amount" is an amount effective to achieve the medically desirable result in the treated subject. The pharmaceutical compositions may contain suitable pharmaceutical acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutical.

The pharmaceutical compositions may be formulated in any acceptable way to meet the needs of the mode of administration. The use of biomaterials and other polymers for drug delivery, as well the different techniques and models to validate a specific mode of administration, are disclosed in literature.

Modifications of the compounds of the invention to improve penetration of the blood-brain barrier would also be useful.

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyloleate or triglycerides.

Aqueous injection suspensions that may contain substances increasing the viscosity of the suspension include, for example, sodium carboxymethyl cellulose, sorbitol, and/or dextran. Optionally, the suspension may also contain stabilizers.

Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight.

The compounds of the present invention may be administered to the patient intravenously in a pharmaceutical acceptable carrier such as physiological saline.

Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

As well known in the medical arts, dosages for any one patient depends upon many factors, including the patient's size, body surface area, age, the particular compound to be administered, sex, time and route of administration, general health, and other drugs being administered concurrently.

All references cited herein are entirely incorporated by reference herein, including all data, tables, figures, and text presented in the cited references.

Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art, as well as the non-limiting following figures and examples describing the basic details and some applications of the invention The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures.

A process for preparing the compounds of Formula (I), in which A is A1, comprises dimerizing the starting indole derivative in the presence of an aldheyde or acetal.

The compounds of the present invention can be prepared for example according to the following general scheme.

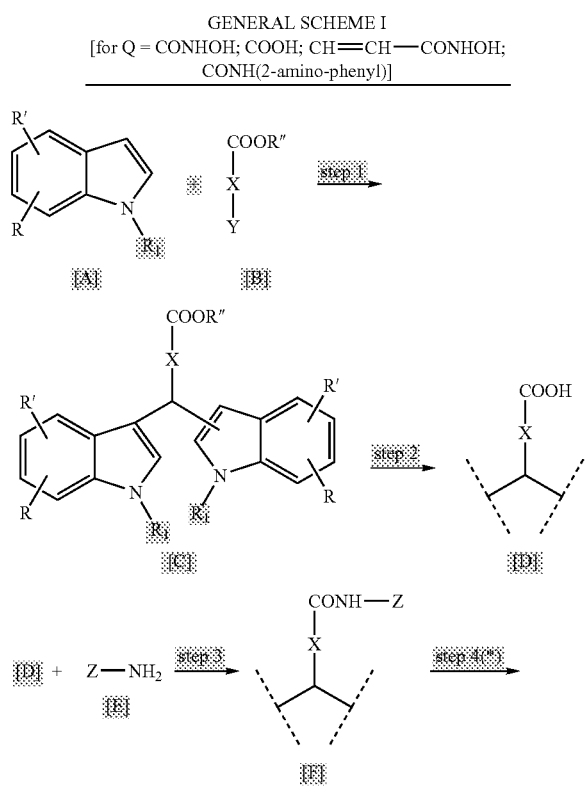

Y = CHO; CH(OR")$_2$
Z = OH; O-benzyl; 2-aminophenyl and
R" is C$_1$-C$_4$ alkyl General Procedure for Step 1:

Step 1 is carried out in organic, polar or non-polar, protic or aprotic solvents, or mixtures of them, i.e. dichloromethane, dichloroethane, acetonitrile, methanol, ethanol, dimethylformamide, water, acetic acid. Reagent B is reacted as free aldehyde or acetale and the reaction is catalysed by organic, inorganic, or Lewis acids, i.e. HCl (Herbert R et al., *J Chem Soc*, 1969, 1505), trifluoroacetic acid [Tominaga Y et al., *Heterocycles*, 2001, 55 (8), 1447-1450], acetic acid (Wang Q M et al., *Synlett*, 1995, 12, 1267-1268), dysprosium triflate [Chen D et al., *Tetrahedron Lett*, 1996, 37 (26), 4467-4470], lithium perclorate [Yadav J S et al, *Synthesis*, 2001, (5), 783-787]. Temperatures from −10° C. to 150° C. are used. Compounds C can be purified by flash silica gel chromatography.

General Procedure for Step 2:

Step 2 is normally carried out in a mixture of water and organic solvents, such as methanol, ethanol, by using an inorganic base such as NaOH, LiOH. After stirring at room temperature, reaction mixture is acidified with HCl 1N and compounds D are purified by extraction with organic solvents, i.e. dichloromethane, ethyl acetate.

General Procedure for Step 3:

Step 3 is carried out in organic, polar or non-polar, aprotic solvents, or mixtures of them, i.e. dichloromethane, dichloroethane, dimethylformamide, tetrahydrofuran, dioxane. Different condensating and/or activating agents can be used, such as DCC, EDC, HOBt, HATU, PyBOP [Lloyd-Williams P., Albericio F. and Giralt E., *Chemical Approaches to the synthesis of peptides and proteins*, (1997) and refs] and the reaction is catalysed by using an organic base, such as N-methylmorfoline, N,N-diisopropylethylamine, triethylamine, DBU [Sandanayaka V P et al., *Tetrahedron Lett*, 2001, 42 (28), 4605-4607. Bailen M A et al., *Tetrahedron Lett*, 2001, 42 (30), 5013-5016]. Temperatures from −10° C. to 100° C. are used. Compounds F are purified by silica gel chromatography or by reversed-phase high performance chromatography (RP-HPLC).

General Procedure for Step 4:

If Z of intermediate F is a O-benzyl group, the reaction is carried out in organic solvents, i.e. methanol, by using hydrogen pressures from 15 psi to 60 psi, and different catalysts such as Pd/C 10%, Pd/BaSO$_4$ 5 or 10% [Nikam S S et al., *Tetrahedron Lett*, 1995, 36 (2), 197-200]. The final products G are purified by solvent evaporation and eventually column chromatography on silica gel or high-performance reversed-phase chromatography.

When Q is —SH the following Scheme II may be followed.

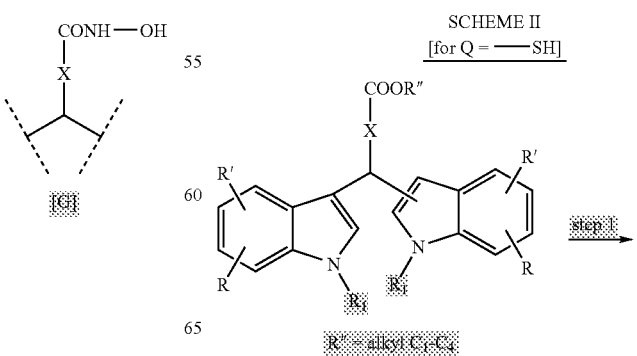

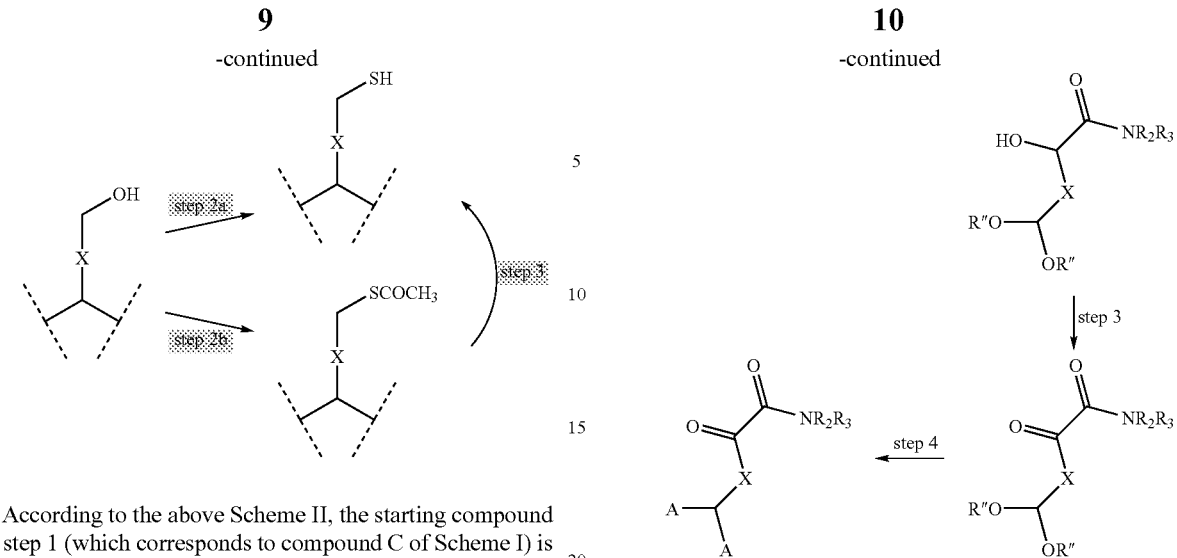

According to the above Scheme II, the starting compound of step 1 (which corresponds to compound C of Scheme I) is treated with $NaBH_4$. According to step 2a the compound obtained through step 1 is reacted with Lawesson's reagent [see Rajagopalan, S. et al., Synth. Comm. 1997, 27 (1), 187-194]. According to step 2b the compound obtained through step 1 is reacted with $CH_3COSH$, DEAD, TPP [see Wisniewski, K. et al., Bioorg. Med. Chem. Lett., 1999 (9), 2801-2804]. In step 3 the compounds obtained through step 2 a or step 2b are treated with NaOH to give the corresponding compounds of Formula I.

When Q is —$COCF_3$ the following Scheme III may be followed.

SCHEME III

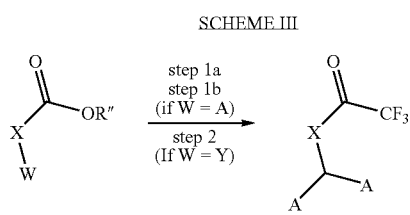

where W=A or Y and R"=$C_1$-$C_4$ alkyl

According to the above Scheme III, the starting compound of step 1a is treated with $(CH_3)_3SiCF_3$ and $NBu_4F$. [see Wiedemann, J. et al., Angew. Chem. Int. Ed., 1998, 37 (6), 820-821]. If step 1b is performed, the starting compound is treated with ClCOCOCl or $SOCl_2$; TFAA, Pyridine [see Boivin, J. et al., Tetrahedron 1995, 51 (9), 2573-2584, or Frey, R. R. et al., Bioorg. Med. Chem. Lett., 2002 (12), 3443-3447].

Step 2 is carried out as step 1 of Scheme I [for Q=CONHOH; COOH; CH=CH—CONHOH; CONH(2-amino-phenyl)]

When Q is —$COCONR_2R_3$ the following Scheme IV may be followed.

SCHEME IV

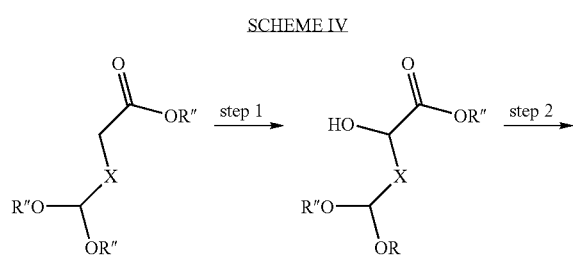

where R" is $C_1$-$C_4$ alkyl

According to the above Scheme IV, the starting compound of step 1 is treated with LiHMDS and Davis' oxaziridine.

According to step 2 the compound obtained through step 1 is reacted with $R_2R_3NH$.

According to step 3 the compound obtained through step 2 is reacted with Dess-Martin periodinane. [Wada, C. K. et al., Bioorg. Med. Chem. Lett., 2003 (13), 3331-3335].

Step 4 is carried out as step 1 in General Scheme I [for Q=CONHOH; COOH; CH=CH—CONHOH; CONH(2-amino-phenyl)].

The following examples further illustrate the invention without limiting its scope.

EXAMPLES

Example 1

Preparation of 7,7-Bis-(1H-indol-3-yl)-heptanoic acid hydroxyamide (ST2741)

Step 1. A solution of B (7-Oxo-heptanoic acid ethyl ester, 274.5 mg, 1.59 mmol), A (1H-Indole, 373.3 mg, 3.18 mmol) and Dysprosium triflate (1.45 g, 2.38 mmol) in $MeOH/H_2O$ (7.5 mL/2.5 mL) was stirred for 36 h at room temperature. Then the reaction mixture was diluted with dichloromethane (DCM) and washed with $H_2O$ (×3 times). The organic layer was dried over sodium sulfate, filtered and evaporated under reduced pressure. The residue was purified by column chromatography on silica gel using a gradient elution of hexane/ethyl acetate to give 0.4 g of C [7,7-Bis-(1H-indol-3-yl)-heptanoic acid ethyl ester, y=65%].

$^1$H-NMR (200 MHz, $CDCl_3$) δ (ppm): 1.30 (t, 3H, $CH_3$); 1.46 (br m, 4H, $CH_2$); 1.66 (br m, 2H, $CH_2$); 2.30 (m, 4H, $CH_2$); 4.18 (q, 2H, $OCH_2$); 4.51 (t, 1H, CH); 6.92 (s, 2H); 7.00-7.40 (m, 6H, CH arom); 7.65 (d, 2H, CH arom); 7.88 (s, 2H).

$^{13}$C-NMR (50 MHz, $CDCl_3$) δ (ppm): 14.48; 25.18; 28.16; 29.47; 34.15; 34.60; 35.87; 60.43; 111.27; 119.07; 119.71; 120.37; 121.61; 121.78; 127.22; 136.67; 174.16.

ES-MS m/z: 411.6 [M+Na]+.

Step 2. To a solution of intermediate C [7,7-Bis-(1H-indol-3-yl)-heptanoic acid ethyl ester, 380 mg, 0.98 mmol] in THF: MeOH: $H_2O$ 3:3:1 (3.8 mL) was added solid NaOH (235 mg, 5.88 mmol) and the reaction mixture was stirred at room temperature for 15 h. The solution was acidified (pH~1) with HCl 1N and then extracted with DCM. The organic layer was washed with $H_2O$ (×3), then dried over sodium sulfate, filtered and evaporated under reduced pressure to give 0.33 g of D [7,7-Bis-(1H-indol-3-yl)-heptanoic acid, ST 3127, y=93%].

$^1$H-NMR (300 MHz, Acetone-$d_6$) δ (ppm): 1.45 (br m, 4H, $CH_2$); 1.59 (quint, 2H, $CH_2$); 2.26 (m, 4H, $CH_2$); 4.52 (t, 1H, CH); 6.87-6.95 (m, 2H, CHarom); 6.99-7.07 (m, 2H, CHarom); 7.21 (d, 2H, CHarom); 7.34 (d, 2H, CHarom); 7.59 (d, 2H, CHarom); 9.89 (s, 2H, NH).

$^{13}$C-NMR (75 MHz, Acetone-$d_6$) δ (ppm): 25.06; 28.14; 29.29; 33.57; 34.19; 35.81; 111.39; 118.42; 119.50; 119.95; 121.16; 121.99; 127.56; 137.39; 174.02.

ES-MS m/z: 359.2 [M−H]$^−$ and 383.2 [M+Na]$^+$.

Step 3. To a solution of intermediate D [7,7-Bis-(1H-indol-3-yl)-heptanoic acid, 140 mg, 0.388 mmol] and PyBOP (259.5 mg, 0.465 mmol) in DCM (1 mL) were added NMM (0.213 mL, 1.94 mmol) and E (O-benzylhydroxylamine hydrochloride, 74.3 mg, 0.465 mmol). The solution was stirred at room temperature for 2.5 h, then diluted with ethyl acetate and washed with $H_2O$ (x 3). The organic layer was dried over sodium sulfate, filtered and evaporated under reduced pressure. The residue was purified by a preparative TLC on silica gel using hexane/ethyl acetate 7:3 as eluent system, to give 0.12 g of F [7,7-Bis-(1H-indol-3-yl)-heptanoic acid benzyloxy-amide, y=70%].

$^1$H-NMR (300 MHz, Acetone-$d_6$) δ (ppm): 1.41 (br m, 4H, $CH_2$); 1.57 (quint, 2H, $CH_2$); 2.02 (br m, 2H, $CH_2$); 2.26 (q, 2H, $CH_2$); 4.49 (t, 1H, CH); 4.84 (s, 2H, $CH_2$); 6.89 (m, 2H, CHarom); 7.01 (m, 2H, CHarom); 7.21 (s-d, [J=1.59 Hz], 2H, CH); 7.28-7.42 (m, 7H, CHarom); 7.57 (d, 2H, CHarom); 9.92 (br s, 2H, NH).

$^{13}$C-NMR (75 MHz, Acetone-$d_6$) δ (ppm): 25.46; 28.13; 29.29; 32.91; 34.17; 35.81; 77.46; 111.32; 111.37; 118.34; 119.47; 119.94; 121.10; 121.81; 121.96; 127.52; 127.55; 128.35; 128.42; 129.12; 137.32; 161.09.

ES-MS m/z: 464.4 [M−H]$^−$ and 488.5 [M+Na]$^+$.

Step 4. Palladium on activated carbon (10%, cat.) was added to a solution of intermediate F [7,7-Bis-(1H-indol-3-yl)-heptanoic acid benzyloxy-amide, 79 mg, 0,170 mmol] in MeOH (4 mL). After 6 h of stirring under hydrogen atmosphere (15 psi) the reaction mixture was filtered and the filtrate was evaporated under reduced pressure. The residue was purified by preparative reversed-phase chromatography (column Lichrosorb RP-18, 7 μm, eluents: $CH_3CN/H_2O$ 1:1, flow=10 mL/min) gave 50.0 mg of G [7,7-Bis-(1H-indol-3-yl)-heptanoic acid hydroxyamide, ST 2741, y=78%].

$^1$H-NMR (300 MHz, Acetone-$d_6$) δ (ppm): 1.42 (br, 4H, $CH_2$); 1.57 (quint, 2H, $CH_2$); 2.06 (br, 2H, $CH_2$); 4.48 (t, 1H, CH); 6.89 (m, 2H, CH arom); 6.99 (m, 2H, CH arom); 7.20 (s, 2H, CH arom); 7.33 (d, 2H, CH arom); 7.57 (d, 2H, CH arom); 9.92 (br, 2H, NH).

$^{13}$C-NMR (75 MHz, Acetone-$d_6$) δ (ppm): 24.66; 31.65; 33.22; 34.84 (some signals under solvent signal); 110.37; 117.32; 118.45; 118.89; 120.09; 120.80; 120.94; 126.50; 136.28; 169.81.

ES-MS m/z: 374.4 [M−H]$^−$.

Example 2

Preparation of 5,5-Bis-(1H-indol-3-yl)-pentanoic acid hydroxyamide (ST2743)

Step 1. A solution of A (1H-Indole, 1.12 g, 9.75 mmol), B [5,5-Dimethoxy-pentanoic acid methyl ester; 521.3 mg, 2.96 mmol] and Dysprosium triflate (2.64 g, 4.33 mmol) in MeOH/$H_2O$ (6 mL/4 mL) reacted as in example 1 (at 60° C.) to give 0.74 g of C [5,5-Bis-(1H-indol-3-yl)-pentanoic acid methyl ester, y=72%].

$^1$H-NMR (200 MHz, CDCl$_3$) δ (ppm): 1.78 (m, 2H, $CH_2$); 2.28 (q, 2H, $CH_2$); 2.41 (t, 2H, $CH_2$); 3.68 (s, 3H, $CH_3$); 4.53 (t, 1H, CH); 6.95 (s, 2H); 7.00-7.32 (m, 6H, CH arom); 7.63 (d, 2H, CH arom); 7.89 (s, 2H, NH).

$^{13}$C-NMR (50 MHz, CDCl$_3$) δ (ppm): 23.84; 34.02; 34.26; 35.28; 51.65; 111.25; 119.13; 119.64; 119.88; 121.69; 121.84; 127.11; 136.68; 174.40.

ES-MS m/z: 369.5 [M+Na]$^+$.

Step 2. Intermediate C [5,5-Bis-(1H-indol-3-yl)-pentanoic acid methyl ester, 495 mg, 1.43 mmol] and solid NaOH (457 mg, 11.4 mmol) in MeOH/DCM (3 mL/1 mL) reacted as in example 1 to give 0.45 g of D [5,5-Bis-(1H-indol-3-yl)-pentanoic acid, y=95%].

$^1$H-NMR (200 MHz, CDCl$_3$) δ (ppm): 1.78 (m, 2H, $CH_2$); 2.28 (q, 2H, $CH_2$); 2.41 (t, 2H, $CH_2$); 4.53 (t, 1H, CH); 6.95 (s, 2H); 7.00-7.36 (m, 6H, CH arom); 7.63 (d, 2H, CH arom); 7.89 (s, 2H, NH).

$^{13}$C-NMR (50 MHz, CDCl$_3$) δ (ppm): 23.58; 33.96; 34.18; 35.17; 111.29; 119.14; 119.61; 119.76; 121.71; 121.85; 122.04; 127.07; 136.64; 179.85.

ES-MS m/z: 331.4 [M−H]$^−$.

Step 3. A solution of intermediate D [5,5-Bis-(1H-indol-3-yl)-pentanoic acid, 202 mg, 0.608 mmol], PyBOP (406.2 mg, 0.73 mmol), NMM (0.33 mL, 3.04 mmol) and E (O-benzylhydroxylamine hydrochloride, 116.5 mg, 0.73 mmol) in DCM (4 mL) reacted in the same conditions of example 1 to give 0.16 g of F [5,5-Bis-(1H-indol-3-yl)-pentanoic acid benzyloxy-amide, y=60%].

$^1$H-NMR (200 MHz, CDCl$_3$) δ (ppm): 1.78 (m, 2H, $CH_2$); 2.07 (br, 2H, $CH_2$); 2.20 (m, 2H, $CH_2$); 4.48 (t, 1H, CH); 4.86 (s, 2H, $CH_2O$); 6.97-7.22 (m, 6H, CH arom); 7.27-7.43 (br, 2H, CH arom); 7.56 (d, 2H, CH arom); 8.08 (s, 2H, NH).

ES-MS m/z: 436.4 [M−H]$^−$ and 460.3 [M+Na]$^+$.

Step 4. The reaction of intermediate F [5,5-Bis-(1H-indol-3-yl)-pentanoic acid benzyloxy-amide, 132 mg, 0.30 mmol] was carried out as in example 1 to give 0.10 g of G [5,5-Bis-(1H-indol-3-yl)-pentanoic acid hydroxyamide, ST 2743, y=97%].

$^1$H-NMR (300 MHz, CD$_3$OH) δ (ppm): 1.69 (br quint, 2H, $CH_2$); 2.22 (br m, 4H, $CH_2$); 4.44 (t, 1H, CH); 6.86 (m, 2H, CH arom); 7.00 (t, 2H, CH arom); 7.20 (m, 4H, CH arom); 7.27 (d, 2H, CH arom); 7.47 (d, 2H, CH arom).

$^{13}$C-NMR (75 MHz, CD$_3$OH) δ (ppm): 25.80; 35.22; 36.45; 36.62; 112.11; 119.18; 120.24; 120.42; 122.08; 122.84; 128.41; 138.40; 179.45.

ES-MS m/z: 346.4 [M−H]$^−$.

Example 3

Preparation of 6,6-Bis-(1H-indol-3-yl)-hexanoic acid hydroxyamide (ST2754)

ST 2754 was synthesised as described in example 1.

Step 1. A solution of A (1H-Indole, 740 mg, 6.32 mmol), B [6-Oxo-hexanoic acid ethyl ester; 500 mg, 3.16 mmol] and Dysprosium triflate (2.89 g, 4.74 mmol) in MeOH/$H_2O$ (13 mL/8 mL) reacted as in example 1 (at 65° C.) to give 0.60 g of C [6,6-Bis-(1H-indol-3-yl)-hexanoic acid ethyl ester, y=50%].

$^1$H-NMR (200 MHz, CDCl$_3$) δ (ppm): 1.25 (t, 3H, $CH_3$); 1.48 (m, 2H, $CH_2$); 1.74 (q, 2H, $CH_2$); 2.28 (m, 4H, $CH_2$); 4.13 (q, 2H, $CH_2$); 4.50 (t, 1H, CH); 6.94 (s, 2H); 7.02-7.40 (m, 6H, CH arom); 7.63 (d, 2H, CH arom); 7.91 (s, 2H, NH).

$^{13}$C-NMR (50 MHz, CDCl$_3$) δ (ppm): 14.33; 25.26; 27.94; 34.02; 34.49; 35.58; 60.34; 111.24; 119.11; 119.71; 120.27; 121.60; 121.83; 127.20; 136.70; 174.12.

ES-MS m/z: 375.6 [M+H]$^+$.

Step 2. Intermediate C [6,6-Bis-(1H-indol-3-yl)-hexanoic acid ethyl ester], 300 mg, 0.80 mmol] and solid NaOH (400 mg, 9.6 mmol) in MeOH/DCM (4 mL/0.5 mL) reacted as in example 1 to give 0.27 g of D [6,6-Bis-(1H-indol-3-yl)-hexanoic acid, y=97%].

$^1$H-NMR (200 MHz, CDCl$_3$) δ (ppm): 1.48 (m, 2H, CH$_2$); 1.71 (m, 2H, CH$_2$); 2.29 (m, 4H, CH$_2$); 4.50 (t, 1H, CH); 6.90-7.40 (m, 8H, CH arom); 7.63 (d, 2H, CH arom); 7.90 (s, 2H, NH).

$^{13}$C-NMR (50 MHz, CDCl$_3$) δ (ppm): 15.35; 24.91; 27.82; 34.01; 35.44; 111.20; 119.15; 119.70; 120.24; 121.54; 121.87; 127.17; 136.69; 179.48.

ES-MS m/z: 345.5 [M−H]$^-$.

Step 3. A solution of intermediate D [6,6-Bis-(1H-indol-3-yl)-hexanoic acid, 232 mg, 0.69 mmol], PyBOP (422.2 mg, 0.76 mmol), NMM (0.38 mL, 3.45 mmol) and E (O-benzylhydroxylamine hydrochloride, 121.1 mg, 0.76 mmol) in DCM (3 mL) reacted in the same conditions of example 1 to give 0.19 g of F [6,6-Bis-(1H-indol-3-yl)-hexanoic acid benzyloxy-amide, y=62%].

$^1$H-NMR (200 MHz, CDCl$_3$) δ (ppm): 1.32 (br, 2H, CH$_2$); 1.63 (m, 2H, CH$_2$); 1.86 (br, 2H, CH$_2$); 2.17 (m, 2H, CH$_2$); 4.43 (t, 1H, CH); 4.78 (s, 2H, CH$_2$O); 6.80-7.20 (m, 6H, CH arom); 7.33 (s, 5H, CH arom); 7.58 (d, 2H, CH arom); 7.95 (s, 2H, NH).

$^{13}$C-NMR (50 MHz, CDCl$_3$) δ (ppm): 25.46; 27.71; 32.99; 33.95; 35.37; 60.54; 111.30; 119.07; 119.64; 119.87; 120.09; 120.80; 121.68; 121.81; 127.12; 128.72; 129.34; 136.66; 161.09.

ES-MS m/z: 452.7 [M+H]$^+$.

Step 4. The reaction of intermediate F [6,6-Bis-(1H-indol-3-yl)-hexanoic acid benzyloxy-amide, 162.7 mg, 0.36 mmol] was carried out as in example 1 to give 67 mg of G [6,6-Bis-(1H-indol-3-yl)-hexanoic acid hydroxyamide, ST 2754, y=54%].

$^1$H-NMR (200 MHz, CD$_3$OH) δ (ppm): 1.44 (m, 2H, CH$_2$); 1.69 (m, 2H, CH$_2$); 2.05 (t, 2H, CH); 2.25 (q, 2H, CH$_2$); 4.44 (t, 1H, CH); 6.89 (t, 2H, CH arom); 7.05 (m, 4H, CH arom); 7.31 (d, 2H, CH arom); 7.50 (d, 2H, CH arom).

$^{13}$C-NMR (50 MHz, CD$_3$OH) δ (ppm): 25.03; 27.28; 32.05; 33.35; 34.75; 110.05; 117.65; 118.25; 119.77; 120.08; 120.69; 126.39; 136.20; 179.45.

ES-MS m/z: 360.3 [M−H]$^-$ and 384.3 [M+Na]$^+$.

Example 4

Preparation of N-Hydroxy-4,4-bis-(1H-indol-3-yl)-butyramide (ST2408)

Step 1. A solution of A (1H-Indole, 3.1 g, 26.5 mmol), B [4-Oxo-butyric acid; 4.8 mL, 7.69 mmol] and Dysprosium triflate (1.55 g, 2.5 mmol) in EtOH 95%/H$_2$O (32 mL/16 mL) reacted as in example 1 to give 0.36 g of C [5,5-Bis-(1H-indol-3-yl)-pentanoic acid methyl ester, y=15%].

$^1$H-NMR (200 MHz, DMSO-d$_6$) δ (ppm): 2.28 (m, 2H, CH$_2$); 2.48 (q, 2H, CH$_2$); 4.48 (t, 1H, CH); 6.80-7.16 (m, 6H, CH arom); 7.36 (d, 2H, CH arom); 7.56 (d, 2H, CH arom); 9.20 (s, 2H).

ES-MS m/z: 317.4 [M−H]$^-$.

Step 3. A solution of intermediate D [4,4-Bis-(1H-indol-3-yl)-butyric acid, ST 1961, 220 mg, 0.69 mmol], PyBOP (392 mg, 0.70 mmol), TEA (0.40 mL, 2.77 mmol) and E (O-benzylhydroxylamine hydrochloride, 113 mg, 0.70 mmol) in DCM (40 mL) reacted in the same conditions of example 1 to give 0.20 g of F [N-Benzyloxy-4,4-bis-(1H-indol-3-yl)-butyramide, y=68%].

$^1$H-NMR (200 MHz, CD$_3$OD) δ (ppm): 2.18 (t, 2H, CH$_2$); 2.57 (q, 2H, CH$_2$); 4.43 (t, 1H, CH); 4.80 (s, 2H, CH$_2$O); 6.92 (t, 2H, CH arom); 6.98-7.17 (m, 4H, CH arom); 7.27 (m, 7H, CH arom); 7.56 (d, 2H, CH arom).

$^{13}$C-NMR (50 MHz, CD$_3$OH) δ (ppm): 30.65; 30.74; 33.11; 77.00; 110.25; 117.38; 117.78; 118.34; 120.20; 121.09; 126.39; 127.50; 127.62; 128.34; 135.04; 136.48; 171.18.

ES-MS m/z: 422.3 [M−H]$^-$ and 424.5 [M+H]$^+$.

Step 4. The reaction of intermediate F, [N-Benzyloxy-4,4-bis-(1H-indol-3-yl)-butyramide, 200 mg, 0.47 mmol] was carried out as in example 1 to give 0.11 g of G [N-Hydroxy-4,4-bis-(1H-indol-3-yl)-butyramide, ST 2408, y=71%].

$^1$H-NMR (300 MHz, CD$_3$OH) δ (ppm): 2.20 (t, 2H, CH$_2$); 2.57 (q, 2H, CH$_2$); 4.46 (t, 1H, CH); 6.95 (t, 2H, CH arom); 6.98-7.19 (m, 4H, CH arom); 7.27 (d, 2H, CH arom); 7.47 (d, 2H, CH arom).

$^{13}$C-NMR (50 MHz, CD$_3$OH) δ (ppm): 30.80; 30.93; 33.19; 110.23; 117.36; 117.87; 118.32; 120.18; 121.05; 126.41; 136.48; 171.31.

ES-MS m/z: 332.4 [M−H]$^-$.

Example 5

Preparation of 8,8-Bis-(1H-indol-3-yl)-octanoic acid hydroxyamide (ST2889)

Step 1. A solution of B (8-Oxo-octanoic acid ethyl ester, 920.0 mg, 4.94 mmol), A (1H-Indole, 1.16 g mg, 9.88 mmol) and Dysprosium triflate (4.5 g, 7.41 mmol) in MeOH/H$_2$O (21 mL/7 mL) reacted in the same conditions of example 1 (16 h at 50° C.) to give 0.4 g of C [8,8-Bis-(1H-indol-3-yl)-octanoic acid ethyl ester, y=23%].

$^1$H-NMR (200 MHz, CDCl$_3$) δ (ppm): 1.31 (t, 3H, CH$_3$); 1.42 (br, 4H, CH$_2$); 1.64 (m, 2H, CH$_2$); 2.30 (m, 4H, CH$_2$); 4.18 (q, 2H, OCH$_2$); 4.51 (t, 1H, CH); 6.95 (s, 2H); 7.10 (t, 2H, CH arom); 7.21 (t, 2H, CH arom); 7.33 (d, 2H, CH arom); 7.66 (d, 2H, CH arom); 7.90 (s, 2H, NH).

$^{13}$C-NMR (50 MHz, CDCl$_3$) δ (ppm): 14.39; 25.13; 28.26; 29.24; 29.53; 34.12; 34.52; 35.94; 60.35; 111.25; 119.08; 119.76; 120.51; 121.60; 121.80; 127.29; 136.73; 174.18.

ES-MS m/z: 401.3 [M−H]$^-$ and 425.5 [M+Na]$^+$.

Step 2. The reaction of intermediate C [8,8-Bis-(1H-indol-3-yl)-octanoic acid ethyl ester, 340 mg, 0.846 mmol] and solid LiOH (177.5 mg, 4.23 mmol) in MeOH/H$_2$O (2.9 mL/0.3 mL) was carried out as in example 1 to give 0.3 g of D [8,8-Bis-(1H-indol-3-yl)-octanoic acid, y=95%].

$^1$H-NMR (200 MHz, CDCl$_3$) δ (ppm): 1.39 (br, 6H, CH$_2$); 1.62 (quint, 2H, CH$_2$); 2.24 (m, 2H, CH$_2$); 2.33 (t, 2H, CH$_2$); 4.49 (t, 1H, CH); 6.98 (s, 2H, CHarom); 7.07 (t, 2H, CHarom); 7.18 (t, 2H, CHarom); 7.34 (d, 2H, CHarom); 7.63 (d, 2H, CHarom); 7.86 (s, 2H, NH).

$^{13}$C-NMR (50 MHz, CDCl$_3$) δ (ppm): 24.75; 28.16; 29.08; 29.42; 34.02; 34.11; 35.82; 111.17; 119.11; 119.75; 120.54; 121.50; 121.83; 127.26; 136.70; 179.73.

ES-MS m/z: 373.0 [M−H]$^-$ and 397.4 [M+Na]$^+$.

Step 3. In a flask reagent E (hydroxylamine hydrochloride, 56.0 mg, 0.80 mmol) and DBU (122.6 mg, 0.80 mmol) were dissolved in DMF (0.8 mL) and the resulting solution was added to a solution of intermediate D [8,8-Bis-(1H-indol-3-yl)-octanoic acid, 200 mg, 0.537 mmol], HATU (224.6 mg, 0.591 mmol) and DIEA (187.1 μL, 1.07 mmol). The reaction mixture was stirred at room temperature for 30 min and then diluted with ethyl acetate. The organic layer was washed with H$_2$O (×3), dried over sodium sulfate, filtered and evaporated under reduced pressure. The residue was purified by a column chromatography on silica gel using a gradient elution of DCM/MeOH to give 0.12 g of F [8,8-Bis-(1H-indol-3-yl)-octanoic acid hydroxamide, ST 2889, y=57%).

$^1$H-NMR (300 MHz, DMSO-$d_6$) δ (ppm): 1.14-1.28 (br m, 6H, $CH_2$); 1.41 (quint, 2H, $CH_2$); 1.87 (t, 2H, $CH_2$); 2.13 (br, 2H, $CH_2$); 4.32 (t, 1H, CH); 6.83 (t, 2H, CH arom); 6.96 (t, 2H, CH arom); 7.18 (s, 2H, CH arom); 7.26 (d, 2H, CH arom); 7.46 (d, 2H, CH arom); 8.59 (s, 1H); 10.26 (s, 1H); 10.68 (s, 2H, NH).

$^{13}$C-NMR (75 MHz, DMSO-$d_6$) δ (ppm): 25.83; 28.48; 29.35; 29.48; 32.93; 34.09; 35.73; 110.95; 118.51; 119.57; 119.65; 121.21; 122.52; 127.37; 137.14; 169.80.

ES-MS m/z: 388.2 [M−H]⁻ and 412.7 [M+Na]⁺.

Example 6

Preparation of 7,7-Bis-(7-methoxy-1H-indol-3-yl)-heptanoic acid hydroxyamide (ST3043)

Step 1. A solution of B (7-Oxo-heptanoic acid ethyl ester, 58 mg, 0.34 mmol), A (7-Methoxy-1H-indole, 100 mg, 0.68 mmol) and trifluoroacetic acid (0.03 mmol mmol) in $CH_3CN$ (1 mL) was stirred for 72 h at room temperature, then the solvent was evaporated under reduced pressure. Compound C [7,7-Bis-(7-methoxy-1H-indol-3-yl)-heptanoic acid ethyl ester] was not isolated and was characterised by ES-MS (m/z: 449.6 [M+H]⁺).

Step 2. The crude of intermediate C [7,7-Bis-(7-methoxy-1H-indol-3-yl)-heptanoic acid ethyl ester], obtained from step 1 reacted with solid LiOH (43 mg, 1.02 mmol) in MeOH/THF/$H_2O$ 3:3:1 (2 mL) as described in example 1 to give product D [7,7-Bis-(7-methoxy-1H-indol-3-yl)-heptanoic acid], that was not isolated and was characterised by ES-MS (m/z: 419.4 [M−H]⁻).

Step 3. The crude of intermediate D [7,7-Bis-(7-methoxy-1H-indol-3-yl)-heptanoic acid] of step 2 reacted with PyBOP (265.2 mg, 0.51 mmol), DIEA (0.30 mL, 1.7 mmol) and E (O-benzylhydroxylamine hydrochloride, 271.3 mg, 1.7 mmol) in DCM (2 mL) as in example 1 to give F [7,7-Bis-(7-methoxy-1H-indol-3-yl)-heptanoic acid benzyloxy-amide]; ES-MS (m/z: 526.8 [M+H]⁺).

Step 4. The intermediate F [7,7-Bis-(7-methoxy-1H-indol-3-yl)-heptanoic acid benzyloxy-amide] obtained from step 3 was dissolved in MeOH and Pd/$BaSO_4$ 10% (cat) was added. The solution was mechanically stirred under hydrogen atmosphere (55 psi) overnight. The reaction mixture was filtered and the filtrate was evaporated under reduced pressure. The solid residue was purified by preparative RP-HPLC (column Lichrosorb RP-18, 7 □m, eluents: $CH_3CN/H_2O$+0.1% TFA 60: 40) gave 60.0 mg of G [7,7-Bis-(7-methoxy-1H-indol-3-yl)-heptanoic acid hydroxamide, ST 3043, overall yield=40%].

$^1$H-NMR (200 MHz, DMSO-$d_6$) δ (ppm): 1.27 (br, 4H, $CH_2$); 1.42 (m, 2H, $CH_2$); 1.87 (t, 2H, $CH_2$); 2.09 (br, 2H, $CH_2$); 4.27 (t, 1H, CH); 6.56 (d, 2H, CH arom); 6.78 (t, 2H, CH arom); 7.05 (m, 4H, CH arom); 8.63 (s, 1H); 10.29 (s, 1H); 10.79 (s, 2H, NH).

$^{13}$C-NMR (50 MHz, DMSO-$d_6$) δ (ppm): 25.97; 28.37; 29.44; 33.11; 34.32; 35.79; 55.75; 101.96; 112.73; 119.14; 120.20; 122.24; 127.20; 128.96; 146.82; 169.89.

ES-MS m/z: 434.4 [M−H]⁻ and 458.3 [M+Na]⁺.

Example 7

Preparation of 7,7-Bis-(5-methyl-1H-indol-3-yl)-heptanoic acid hydroxyamide (ST3044)

ST 3044 was synthesised as in example 6.

Step 1. Reagent A (5-Methyl-1H-indole, 100 mg, 0.762 mmol) and B [7-Oxo-heptanoic acid ethyl ester, 65.6 mg, 0.381 mmol] reacted to give C [7,7-Bis-(5-methyl-1H-indol-3-yl)-heptanoic acid ethyl ester, that was not isolated and was characterised by ES-MS (m/z: 417.6 [M+H]⁺).

Step 2. The intermediate D [7,7-Bis-(5-methyl-1H-indol-3-yl)-heptanoic acid], not isolated, was characterised by ES-MS (m/z: 387.4 [M−H]⁻).

Step 3. The intermediate F [7,7-Bis-(5-methyl-1H-indol-3-yl)-heptanoic acid benzyloxy-amide] was purified by a flash chromatography on silica gel with a gradient elution of hexane/ethyl acetate and characterised by ES-MS (m/z: 494.7 [M+H]⁺).

Step 4. Product G [7,7-Bis-(5-methyl-1H-indol-3-yl)-heptanoic acid hydroxyamide, ST3044] was purified by filtration of reaction mixture and solvent evaporation under reduced pressure (55 mg, overall yield=36%).

$^1$H-NMR (300 MHz, DMSO-$d_6$) δ (ppm): 1.27 (br, 4H, $CH_2$); 1.42 (m, 2H, $CH_2$); 1.88 (t, 2H, $CH_2$); 2.09 (br, 2H, $CH_2$); 2.28 (s, 3H, $CH_3$); 4.25 (t, 1H, CH); 6.79 (d, 2H, CH arom); 7.09 (s, 2H, CH arom); 7.15 (d, 2H, CH arom); 7.25 (s, 2H, CH arom); 8.61 (s, 1H); 10.27 (s, 1H); 10.53 (s, 2H, NH).

$^{13}$C-NMR (75 MHz, DMSO-$d_6$) δ (ppm): 22.03; 25.93; 28.37; 29.39; 33.04; 34.39; 35.75; 111.69; 119.00; 119.23; 122.64; 122.85; 126.77; 127.58; 135.56; 169.82.

ES-MS m/z: 402.4 [M−H]⁻ and 426.4 [M+Na]⁺.

Example 8

Preparation of 7,7-Bis-(4-fluoro-1H-indol-3-yl)-heptanoic acid hydroxyamide (ST3052)

ST 3052 was synthesised as in example 6.

Step 1. Reagent A (4-Fluoro-1H-indole, 100 mg, 0.74 mmol) and B [7-Oxo-heptanoic acid ethyl ester, 63.7 mg, 0.37 mmol] reacted to give C [7,7-Bis-(4-fluoro-1H-indol-3-yl)-heptanoic acid ethyl ester], that was not isolated and was characterised by ES-MS (m/z: 425.6 [M+H]⁺).

Step 2. The intermediate D [7,7-Bis-(4-fluoro-1H-indol-3-yl)-heptanoic acid] was not isolated and was characterised by ES-MS (m/z: 395.4 [M−H]⁻).

Step 3. The intermediate F [7,7-Bis-(4-fluoro-1H-indol-3-yl)-heptanoic acid benzyloxy-amide] was roughly purified by a flash chromatography on silica gel with a gradient elution of hexane/ethyl acetate and characterised by ES-MS (m/z: 502.7 [M+H]⁺).

Step 4. Product G [7,7-Bis-(4-fluoro-1H-indol-3-yl)-heptanoic acid hydroxyamide, ST 3052] was purified by filtration of reaction mixture, solvent evaporation and preparative RP-HPLC (column Lichrosorb RP-18, 7 μm; eluents: $H_2O/CH_3CN$ 50:50; flow=10 mL/min, 55 mg, overall yield=35%).

$^1$H-NMR (300 MHz, DMSO-$d_6$) δ (ppm): 1.29 (br, 4H, $CH_2$); 1.42 (quint, 2H, $CH_2$); 1.87 (t, 2H, $CH_2$); 2.03 (q, 2H, $CH_2$); 4.67 (t, 1H,CH); 6.58-6.66 (m, 2H, CH arom); 6.98 (m, 4H, CH arom); 7.13 (d, 2H, CH arom); 8.60 (s, 1H); 10.27 (s, 1H); 11.01 (s, 2H, NH).

$^{13}$C-NMR (75 MHz, DMSO-$d_6$) δ (ppm): 25.87; 28.47; 29.39; 33.01; 35.15; 37.89; 103.98 (d, 1C arom, J=19.6 Hz); 108.59; 115.75 (d, 1C arom J=19.0 Hz); 118.89 (d, 1C arom, J=3.97 Hz); 121.80 (d, 1C arom, J=7.95 Hz); 123.12; 139.97 (d, 1C arom, J=12.0 Hz); 157.11 (d, 1C, C—F, J=243.7 Hz); 169.78.

ES-MS m/z: 410.5 [M−H]⁻; 434.4 [M+Na]⁺ and 450.4 [M+K]⁺.

Example 9

Preparation of 3-{4-[Bis-(1H-indol-3-yl)-methyl]-phenyl}-N-hydroxy-acrylamide (ST2887)

Step 1. The reaction of A (1H-Indole, 234 mg, 2 mmol) and B [3-(4-Formyl-phenyl)-acrylic acid, 176 mg, 1 mmol] was carried out as in example 1 to obtain the acid C [3-{4-[Bis-(1H-indol-3-yl)-methyl]-phenyl}-acrylic acid] utilised as crude for step 2.

¹H-NMR (200 MHz, DMSO-d₆) δ (ppm): 5.86 (s, 1H, CH); 6.44 (d, 1H, CH J=16.1 Hz); 6.86 (m, 4H, CHarom); 7.04 (t, 2H, CHarom); 7.25-7.59 (m, 9H, 8CH arom+1 CH double bond); 10.85 (s, 2H, NH).

¹³C-NMR (50 MHz, DMSO-d₆) δ (ppm): 57.58; 112.24; 118.24; 118.98; 119.79; 121.68; 124.36; 127.28; 128.87; 129.56; 132.62; 137.32; 144.68; 148.30; 168.38.

ES-MS m/z: 391.15 [M−H]⁻.

Step 2. The reaction was carried out as in Step 3 of example 3. Purification by preparative RP-HPLC (column Lichrosorb RP-18, 7 µm; eluents: H₂O/CH₃CN 50:50; flow=10 mL/min) gave the product F [3-{4-[Bis-(1H-indol-3-yl)-methyl]-phenyl}-N-hydroxy-acrylamide, ST 2887].

¹H-NMR (300 MHz, DMSO-d₆) δ (ppm): 5.85 (s, 1H, CH); 6.39 (d, 1H, CH J=15.95 Hz); 6.86 (m, 4H, CH arom); 7.03 (t, 2H, CH arom); 7.25-7.48 (m, 9H, 8CH arom+1CH double bond); 8.99 (s, 1H); 10.71 (s, 1H); 10.85 (s, 2H, NH).

¹³C-NMR (75 MHz, DMSO-d₆) δ (ppm): 57.58; 114.16; 120.28; 120.90; 121.72; 123.60; 126.11; 126.27; 129.23; 130.03; 131.52; 135.13; 139.26; 140.96; 149.35; 165.58.

ES-MS m/z: 405.71 [M−H]⁻.

Example 10

Preparation of 7,7-Bis-(1H-indol-3-yl)-heptanoic acid (2-amino-phenyl)-amide (ST3071)

Step 3. The intermediate D [7,7-Bis-(1H-indol-3-yl)-heptanoic acid, 60 mg, 0.167 mmol] obtained from step 2 in example 1 was dissolved in DCM (1 mL), then PyBOP (95.3 mg, 0.184 mmol) and DIEA (87 µL, 0.50 mmol) were added. After 5 min of stirring the resulting solution was added to a solution of E (2-aminophenylamine; 86 mg, 0.835 mmol) in DCM (1 mL) and the reaction mixture was stirred at room temperature for 2 h. Then the solvent was removed under reduced pressure and the residue dissolved in ethyl acetate. The solution was washed with HCl 0.5N, a saturated solution of NaHCO₃ and water (×2). The organic layer was dried over sodium sulfate, filtered and evaporated under reduced pressure. The residue was roughly purified by a flash chromatography on silica gel by using hexane/ethyl acetate as eluent system, to give F [7,7-Bis-(1H-indol-3-yl)-heptanoic acid (2-amino-phenyl)-amide, ST 3071, 50 mg, y=67%]

¹H-NMR (200 MHz, DMSO-d₆) δ (ppm): 1.36 (br, 4H, CH₂); 1.54 (br m, 2H, CH₂); 2.23 (m, 4H, CH₂); 4.36 (t, 1H, CH); 4.79 (s, 2H, CH₂—O); 6.52 (t, 2H, CH arom); 6.70 (d, 2H, CH arom); 6.80-7.05 (m, 4H, CH arom); 7.06-7.32 (m, 4H, CH arom); 7.50 (d, 2H, CH arom); 9.06 (s, 1H, NH); 10.72 (s, 2H, NH).

¹³C-NMR (50 MHz, DMSO-d₆) δ (ppm): 26.16; 28.45; 29.53; 34.11; 35.70; 36.60; 112.02; 116.60; 116.89; 118.58; 119.57; 119.73; 121.29; 122.61; 124.30; 126.01; 126.40; 127.40; 137.19; 142.62; 171.89.

ES-MS m/z: 451.2 [M+H]⁺ and 449.4 [M−H]⁻.

Example 11

Preparation of N-Hydroxy-3-(1H-indol-3-yl)-acrylamide (ST2913)

Reagent E (hydroxylamine hydrochloride, 112.0 mg, 1.61 mmol) and DBU (254.0 mg, 1.61 mmol) were dissolved in DMF (0.5 mL) and the resulting solution was added to a suspension of D [3-(1H-Indol-3-yl)-acrylic acid, 151 mg, 0.806 mmol], HATU (337.1 mg, 0.887 mmol) and DIEA (281.0 µL, 1.61 mmol) in DMF/DCM (1.5 mL/2 mL). The reaction was treated as described in step 3 of example 3 and the final purification by preparative RP-HPLC (column Lichrosorb RP-18, 7 µm; eluents: H₂O/CH₃CN 70:30; flow=10 mL/min) gave the product F [N-Hydroxy-3-(1H-indol-3-yl)-acrylamide, ST 2913, 70 mg, y=43%].

¹H-NMR (300 MHz, DMSO-d₆) δ (ppm): 6.40 (d, 1H, CH═C, J=15.8 Hz); 7.08-7.22 (m, 2H, CH arom); 7.43 (m, 1H, CH arom); 7.54 (d, 1H, CH═C, J=15.9 Hz); 7.78 (m, 2H, CHarom); 8.82 (s, 1H); 10.42 (s, 1H); 11.53 (s, 1H, NH).

¹³C-NMR (75 MHz, DMSO-d₆) δ (ppm): 112.75; 112.97; 113.56; 120.39; 121.02; 122.87; 125.57; 130.83; 133.40; 138.02; 165.28.

ES-MS m/z: 201.1 [M−H]⁻ and 224.86 [M+Na]⁺.

Example 12

Preparation of N-hydroxy-6-(1H-indol-3-yl)hexanamide (ST2995)

Step 3. In a flask reagent E (hydroxylamine hydrochloride, 120.8 mg, 1.74 mmol) and DIEA (302.6 µL, 1.74 mmol) were dissolved in DMF (0.5 mL) and the resulting solution was added to a solution of D [6-(1H-indol-3-yl)hexanoic acid, 200 mg, 0.869 mmol], HATU (363 mg, 0.956 mmol) and DIEA (302.6 µL, 1.74 mmol) in DMF (2 mL). The reaction mixture was stirred at room temperature for 2 h and then diluted with ethyl acetate. The organic layer was washed with HCl 1N, NaHCO₃ 3%, brine (×2), dried over sodium sulfate, filtered and evaporated under reduced pressure. Precipitation from DCM, filtration and final washings of the precipitate with DCM gave 0.17 g of F [8,8-Bis-(1H-indol-3-yl)-octanoic acid hydroxyamide, ST 2995, y=80%).

¹H-NMR (200 MHz, DMSO-d₆) δ (ppm): 1.33 (m, 2H, CH₂); 1.65 (m, 4H, CH₂); 1.94 (t, 2H, CH₂); 2.66 (t, 2H, CH₂); 6.95 (t, 1H, CH arom); 7.05 (m, 2H, CH arom); 7.32 (d, 1H, CH arom); 7.48 (d, 1H, CH arom); 8.65 (s, 1H); 10.32 (s, 1H); 10.73 (s, 1H).

¹³C-NMR (50 MHz, DMSO-d₆) δ (ppm): 25.32; 25.79; 29.34; 30.39; 33.06; 112.03; 115.34; 118.78; 119.03; 121.49; 122.80; 127.96; 137.05; 169.86.

ES-MS m/z: 245.2 [M−H]⁻ and 247.3 [M+H]⁺ and 269.2 [M+Na]⁺.

Example 13

Preparation of 7,7-Bis-(7-Ethyl-1H-indol-3-yl)-heptanoic acid hydroxyamide (ST3126)

Step 1. A solution of B (7-Oxo-heptanoic acid ethyl ester, 90 mg, 0.516 mmol), A (7-ethyl-1H-Indole, 100.2 mg, 0.688 mmol) and Dysprosium triflate (420 mg, 0.688 mmol) in AcCN (1.2 mL) reacted as in example 1 (at room temperature for 2 days) to give C [7,7-Bis-(7-ethyl-1H-indol-3-yl)-heptanoic acid ethyl ester, that was not isolated and was characterised by ES-MS (m/z: 445.8 [M+H]$^+$).

Step 2. The crude of intermediate C [7,7-Bis-(7-ethyl-1H-indol-3-yl)-heptanoic acid ethyl ester], obtained from step 1 reacted as described in example 6 to give product D [7,7-Bis-(7-ethyl-1H-indol-3-yl)-heptanoic acid], that was not isolated and was characterised by ES-MS (m/z: 415.4 [M−H]$^-$).

Step 3. The crude of intermediate D [7,7-Bis-(7-ethyl-1H-indol-3-yl)-heptanoic acid] obtained from step 2 reacted as described in example 6 to give F [7,7-Bis-(7-ethyl-1H-indol-3-yl)-heptanoic acid benzyloxy-amide], that was not isolated and was characterised by ES-MS (m/z: 522.8 [M+H]$^+$).

Step 4. The crude of intermediate F [7,7-Bis-(7-ethyl-1H-indol-3-yl)-heptanoic acid benzyloxy-amide] obtained from step 3 reacted as described in example 6. Purification by preparative RP-HPLC (column Lichrosorb RP-18, 7 ☐m, eluents: CH$_3$CN/H$_2$0 60: 40) gave 100.0 mg of G [7,7-Bis-(7-ethyl-1H-indol-3-yl)-heptanoic acid hydroxyamide, ST3126, overall yield=67%].

$^1$H-NMR (300 MHz, DMSO-d$_6$) δ (ppm): 1.21 (t, 6H, CH$_3$); 1.28 (br, 4H, CH$_2$); 1.42 (m, 2H, CH$_2$); 1.88 (t, 2H, CH$_2$); 2.14 (br, 2H, CH$_2$); 2.77 (q, 4H, CH$_2$); 4.30 (t, 1H, CH); 6.76-6.81 (m, 4H, CH arom); 7.13 (s, 2H, CH arom); 7.34 (m, 2H, CHarom); 8.60 (s, 1H); 10.26 (s, 1H); 10.63 (s, 2H, NH).

$^{13}$C-NMR (75 MHz, DMSO-d$_6$) δ (ppm): 14.99; 24.29; 25.91; 28.40; 29.41; 33.05; 34.24; 35.68; 111.37; 118.83; 119.91; 120.01; 122.01; 122.17; 127.23; 127.29; 135.66; 135.81; 169.80.

ES-MS m/z: 430.4 [M−H]$^-$ and 454.0 [M+Na]$^+$.

Example 14

Preparation 7,7-Bis-(5-morpholin-4-ylmethyl-3H-indol-3-yl)-heptanoic acid hydroxyamide (ST3307)

Step 1. A solution of B (7-oxo-heptanoic acid ethyl ester, 2.7 g, 15.68 mmol) and A (5-morpholin-4-ylmethyl-3H-indole, 2.8 g, 12.95 mmol) in glacial CH$_3$COOH (20 mL) reacted at reflux overnight to give C 7,7-Bis-(5-morpholin-4-ylmethyl-3H-indol-3-yl)-heptanoic acid ethyl ester, that was not isolated and was characterised by ES-MS (m/z: 587.4 [M+H]$^+$ and 609.4 [M+23]$^+$.

Step 2. The crude of intermediate C 7,7-Bis-(5-morpholin-4-ylmethyl-3H-indol-3-yl)-heptanoic acid ethyl ester, obtained from step 1 reacted as described in example 6 to give product D 7,7-Bis-(5-morpholin-4-ylmethyl-3H-indol-3-yl)-heptanoic acid, that was not isolated and was characterised by ES-MS (m/z: 557.6 [M−H]$^-$).

Step 3. The crude of intermediate D 7,7-Bis-(5-morpholin-4-ylmethyl-3H-indol-3-yl)-heptanoic acid obtained from step 2 reacted as described in example 6 to give F 7,7-Bis-(5-morpholin-4-ylmethyl-3H-indol-3-yl)-heptanoic acid benzyloxy-amide, that was not isolated and was characterised by ES-MS (m/z: 664.9 [M+H]$^+$).

Step 4. The crude of intermediate F 7,7-Bis-(5-morpholin-4-ylmethyl-3H-indol-3-yl)-heptanoic acid benzyloxy-amide obtained from step 3 reacted as described in example 6. Purification by preparative RP-HPLC (column Lichrosorb RP-18, 7 μm, eluents: CH$_3$OH+0.1% TFA/H$_2$O+0.1% TFA=45:55) gave 100.0 mg of G 7,7-Bis-(5-morpholin-4-ylmethyl-3H-indol-3-yl)-heptanoic acid hydroxyamide, ST3307, overall yield=40%].

$^1$H-NMR (300 MHz, DMSO-d$_6$) δ (ppm): 1.28 (bm, 4H, 2×CH$_2$); 1.42 (bm, 2H, CH$_2$); 1.88 (m, 2H, CH$_2$); 2.12 (bm, 2H, CH$_2$); 2.32 (bm, 8H, 4×CH$_2$); 3.34 (bm, 4H, 2×CH$_2$); 3.53 (bm, 8H, 4×CH$_2$) 4.30 (t, J=7.1 Hz, 1H, CH); 6.94 (d, J=8.1 Hz, 2H, CH arom); 7.14 (s, 2H, CH arom); 7.22 (d, J=8.1 Hz, 2H, CH arom); 7.33 (s, 2H, CH arom); 8.63 (bs, 2H); 10.30 (s, 2H); 10.71 (s, 2H, NH).

$^{13}$C-NMR (75.5 MHz, DMSO-d$_6$) δ (ppm): 26.00; 27.90; 28.25; 33.99; 34.62; 35.49; 53.63; 62.29; 67.17; 109.78; 118.51; 121.57; 122.73; 123.94; 127.23; 130.13; 136.36; 170.05.

ES-MS m/z: 574.4 [M+H]$^+$.

Example 15

Preparation 7-(1H-Indol-3-yl)-7-(1H-indol-2-yl)-heptanoic acid hydroxyamide (ST3292)

During synthesis of ST2741, example 1,7-(1H-Indol-3-yl)-7-(1H-indol-2-yl)-heptanoic acid hydroxyamide was obtained as impurity. The product was purified and characterized.

$^1$H-NMR (300 MHz, DMSO-d$_6$) δ (ppm): 1.28 (bm, 4H, 2×CH$_2$); 1.44 (bm, 2H, CH$_2$); 1.43 (bm, 2H, CH$_2$); 1.88 (t, 2H, CH$_2$); 2.12 (bm, 2H, CH$_2$); 4.27 (t, J=7.6 Hz, 1H, CH); 6.23 (s, 1H, CH arom); 6.86 (t, J=7.0 Hz, 2H, CH arom); 6.92 (t, J=7.0 Hz, 1H, CH arom); 7.00 (t, J=7.1 Hz, 1H, CH arom); 7.18-7.24 (m, 2H, CH arom); 7.30 (d, J=8.0 Hz, 1H, CH arom); 7.36 (d, J=7.7 Hz, 1H, CH arom); 7.45 (d, J=7.8 Hz, 1H, CH arom); 8.63 (s, 1H); 10.28 (s, 1H); 10.75 (s, 1H); 10.86 (s, 1H).

$^{13}$C-NMR (75.5 MHz, DMSO-d$_6$) δ (ppm): 25.81; 28.04; 29.26; 33.00; 34.96; 36.51; 98.56; 111.39; 112.05; 117.55; 118.82; 119.07; 119.39; 119.82; 120.53; 121.49; 122.88; 127.14; 128.75; 136.66; 137.02; 144.31; 169.78.

ES-MS m/z: 376.2 [M+H]$^+$, 398.1 [M+Na]$^+$ and 374.2 [M−H]$^-$.

Example 16

Preparation of 7,7-Bis-(1H-indol-3-yl)-heptanoic acid (ST3127)

7,7-Bis-(1H-indol-3-yl)-heptanoic acid (ST3127) was prepared as described in example 1, step 1 and step 2.

$^1$H-NMR (300 MHz, Acetone-d$_6$) δ (ppm): 1.45 (br m, 4H, CH$_2$); 1.59 (quint, 2H, CH$_2$); 2.26 (m, 4H, CH$_2$); 4.52 (t, 1H, CH); 6.87-6.95 (m, 2H, CHarom); 6.99-7.07 (m, 2H, CHarom); 7.21 (d, 2H, CHarom); 7.34 (d, 2H, CHarom); 7.59 (d, 2H, CHarom); 9.89 (s, 2H, NH).

$^{13}$C-NMR (75 MHz, Acetone-d$_6$) δ (ppm): 25.06; 28.14; 29.29; 33.57; 34.19; 35.81; 111.39; 118.42; 119.50; 119.95; 121.16; 121.99; 127.56; 137.39; 174.02.

ES-MS m/z: 359.2 [M−H]$^-$ and 383.2 [M+Na]$^+$.

List of Abbreviations
AcCN Acetonitrile
DBU 1,8-Diazabicyclo[5.4.0]undec-7-ene DCC Dicycloexylcarbodiimide
DCM Dichloromethane
DIEA N,N,N-diisopropylethylamine
DMAP 4-Dimethylaminopyridine
DMF Dimethylformamide
DMSO Dimethylsulfoxide
EDC 1-(3-Dimethylaminopropyl)-3-ethylcarbodiimide hydrochloride
EtOH Ethanol
TEA Triethylamine HATU Hydroxyazabenzotriazol-N,N,N,N-tetramethyluronium hexafluorophosphate
HOBt Hydroxybenzotriazole
MeOH Methanol
NMM N-Methylmorpholine
PyBOP (Benzotriazole-1-yl-oxy-tris-pyrrolidino-phosphonium hexafluorophosphate
RP-HPLC Reversed Phase-HPLC
TFA trifluoroacetic acid
THF Tetrahydrofuran
Biological Results
Cytotoxicity Studies To test the effects of the compounds on cell growth, NB4 human promyelocytic leukaemia, NCI-H460 non-small cell carcinoma cells and HCT-116 human colon carcinoma cells were used. NB4 and NCI-H460 tumour cells were grown RPMI 1640 containing 10% fetal bovine serum (GIBCO), whereas HCT-116 tumour cells were grown in McCoy's 5A containing 10% fetal bovine serum (GIBCO).

Tumour cells were seeded in 96-well tissue culture plates (Corning) at approximately 10% confluence and were allowed to attach and recover for at least 24 h. Varying concentrations of the drugs were then added to each well to calculate their IC50 value (the concentration which inhibits the 50% of cell survival). The plates were incubated for 24 h at 37° C. At the end of the treatment, for NB4 tumour cells in suspension, the procedure was performed as follows: medium culture was removed by centrifugation of the plates at 1600×g for 10 min and the surnatant was removed. 250 μl PBS were added, then the plates were centrifuged at 1600×g for 10 min, the surnatant was removed. 200 μl/well of medium culture RPMI 1640 containing 10% FCS were added and the plates were incubated at 37° C. for other 48 h. The plates were centrifuged again at 1600×g for 10 min, the medium culture was removed and 200 μl PBS and 50 μl of cold 80% TCA were added. The plates were incubated on ice for at least 1 h. TCA was removed, the plates were washed 3 times for immersion in distilled-water and dried on paper and at 40° C. for 5 min. Then 200 μl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min. Then 200 μl Tris 10 mM were added, the plates were kept under stirring for 20 min. The survival cell was determined as optical density by a Multiskan spectrofluorimeter at 540 nm. For the tumour cells in adhesion (NCI-H460 and HCT-116), the procedure was as above mentioned, except that at the end of the treatment, the plates were washed by remotion of the surnatant and addition of PBS 3 times without centrifugation. Also the last day of the assay, the surnatant was removed without centrifugation.

The amount of cells killed was calculated as the percentage decrease in sulphorodamine B binding compared with control cultures. The $IC_{50}$ values (the concentration which inhibits the 50% of cell survival) were calculated with the "ALLFIT" program. In the table 1 the cytotoxicity evaluated on NB4 tumor cells showed that ST3044 was the most potent compound with an IC50 value of 0.15 μM followed by other molecules (ST3052, ST3043, ST3292, ST3307, ST2741, ST2887, ST2889, ST2754) with IC50 values of 0.4-2.3 μM. On NCI-H460 non-small cell lung cancer and HCT-116 colon cancer, ST3044, ST3043 and ST3052 were the most potent molecules with IC50 values which ranged from 0.27 to 0.7 μM, followed by ST3292, ST3307, ST2741, ST2887, ST2889, ST2754 with IC50 values of 0.6-5.8 μM. Other molecules (ST2408, ST2743, ST2995, ST3127) showed a minor cytotoxicity on NB4 or NCI-H460 and HCT-116 tumor cells, since IC50 values ranged from 8.8 μM to 88.8 μM.

Moreover, the molecules of the present invention resulted to be more potent than the homologues bis-heterocyclic compounds in the cytotoxicity test on NB4 tumor cells (see Table 2).

TABLE 1

Cytotoxicity of different compounds on NB4, NCI-H460 and HCT-116 tumour cells

| Compound | NB4 | NCI-H460 | HCT-116 |
|---|---|---|---|
| | IC50 ± SD, μM | | |
| ST2408 | 14.6 ± 0.6 | 25.9 ± 0.3 | |
| ST2741 | 0.6 ± 0.01 | 1.2 ± 0.1 | 0.6 ± 0.02 |
| ST2743 | | 88.8 ± 2.8 | |
| ST2754 | 1.6 ± 0.06 | 5.2 ± 0.3 | 5.8 ± 0.2 |
| ST2887 | 0.6 ± 0.01 | 2.6 ± 0.3 | 3.9 ± 0.5 |
| ST2889 | 2.3 ± 0.1 | 2.7 ± 0.2 | 3.5 ± 0.2 |
| ST2995 | 8.8 ± 0.5 | 22 ± 1.7 | |
| ST3043 | 0.8 ± 0.01 | 0.55 ± 0.03 | 0.41 ± 0.03 |
| ST3044 | 0.15 ± 0.02 | 0.51 ± 0.1 | 0.27 ± 0.01 |
| ST3052 | 0.6 ± 0.09 | 0.7 ± 0.09 | 0.4 ± 0.1 |
| ST3127 | >20 | >20 | >20 |
| ST3292 | 0.67 ± 0.01 | 0.82 ± 0.07 | |
| ST3307 | 0.42 ± 0.02 | 1.1 ± 0.1 | |

TABLE 2

Cytotoxicity of the homologues bis-heterocyclic compounds on NB4 tumour cells

| Compound | NB4 IC50 ± SD, μM |
|---|---|
| ST1346 | 44.3 ± 0.6 |
| ST1383 | 48 ± 11 |
| ST1393 | 16.2 ± 0.3 |
| ST1422 | 47.3 ± 5.6 |
| ST1730 | 5.7 ± 0.2 |
| ST1880 | 22 ± 6 |
| ST1896 | 33.6 ± 6.5 |

The invention claimed is:

1. A compound of Formula (I),

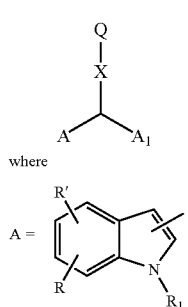

where $A = $ 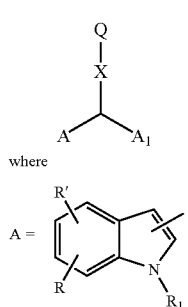

$A_1$ is equal to A, wherein R, R' and $R_1$ are the same for both indole rings;

X is a saturated or unsaturated (alkenylene or alkynylene), linear or branched $(C_3-C_{10})$ alkylene;

$Q=COCONR_2R_3$, or $COCF_3$, or

Q=CONHOG, or 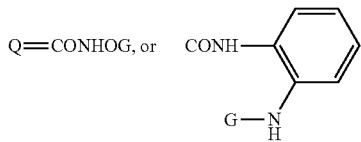

where,

G is either H or a glycosyl;

$R_2$, $R_3$ are the same or different and are either H or a $(C_1-C_4)$ alkyl;

$R_1$ is selected from the group consisting of H, $(C_1-C_4)$ alkyl, $(C_6-C_{12})$ aryl, $(C_6-C_{12})$ aryl-$(C_1-C_4)$ alkylene, $(C_1-C_4)$ alkanoyl and $(C_1-C_4)$-alkyl-$(C_6-C_{10})$-arylene;

R and R', the same or different, are selected from the group consisting of:

H saturated or unsaturated, linear or branched $(C_1-C_{10})$ alkyl, optionally substituted with a $(C_3-C_{10})$ heteroaryl or $(C_3-C_{10})$ heterocyclyl-$(C_1-C_4)$ alkylene, where the heterocycle contains at least one heteroatom selected from N, O or S, or with a group —$NR_5R_6$, where $R_5$, $R_6$ are the same or different and are H, linear or branched $(C_1-C_4)$ alkyl, or $(C_1-C_4)$-alkanoyl $OR_4$ where $R_4$=H, $(C_1-C_4)$ alkyl, mesyl, tosyl, $(C_1-C_4)$ alkanoyl, or glycosyl halogen, azide, nitro, nitrile and $NR_5R_6$.

2. The compound according to claim 1, wherein Q is CONHOG.

3. The compound according to claim 1, wherein G, $R_1$, $R_2$ and $R_3$ are the same and are H.

4. The compound according to claim 1, wherein R and R' are the same and are selected form the group consisting of H, $(C_1-C_3)$ alkylamine and $(C_1-C_3)$ alkylmorpholine.

5. The compound of Formula (I) of claim 1, which is selected from the group consisting of:

5,5-Bis-(1H-indol-3-yl)-pentanoic acid hydroxyamide,
6,6-Bis-(1H-indol-3-yl)-hexanoic acid hydroxyamide,
7,7-Bis-(1H-indol-3-yl)-heptanoic acid hydroxyamide,
7,7-Bis-(4-fluoro-1H-indol-3-yl)-heptanoic acid hydroxyamide,
7,7-Bis-(5-methyl-1H-indol-3-yl)-heptanoic acid hydroxyamide,
7,7-Bis-(7-ethyl-1H-indol-3-yl)-heptanoic acid hydroxyamide,
7,7-Bis-(7-methoxy-1H-indol-3-yl)-heptanoic acid hydroxyamide,
7,7-Bis-(5-morpholin-4-ylmethyl-3H-indol-3-yl)-heptanoic acid hydroxyamide,
7-(1H-Indol-3-yl)-7-(1H-indol-2-yl)-heptanoic acid hydroxyamide, and
7,7-Bis-(1H-indol-3-yl)-heptanoic acid, and
8,8-Bis-(1H-indol-3-yl)-octanoic acid hydroxyamide.

6. A medicament comprising a compound of claim 1.

7. A pharmaceutical composition containing as active ingredient a compound of claim 1 and at least one pharmaceutically acceptable excipient and/or diluent.

8. The pharmaceutical composition according to claim 7 further comprising one or more known antitumor agents.

9. The pharmaceutical composition according to claim 8, in which the known antitumor agent is selected from the group consisting of alkylating agents, topoisomerase inhibitors, antitubulin agents, intercalating compounds, antimetabolites, natural products such as vinca alkaloids, epipodophyllotoxins, antibiotics, enzymes, taxans, and cytodifferentiating compounds.

10. The pharmaceutical composition according to claim 9, in which the cytodifferentiating antitumor compound is all-trans retinoic acid.

* * * * *